US007148066B2

(12) United States Patent
Bickett et al.

(10) Patent No.: US 7,148,066 B2
(45) Date of Patent: Dec. 12, 2006

(54) DYE SOLUTIONS FOR USE IN METHODS TO DETECT THE PRIOR EVAPORATION OF ANHYDROUS AMMONIA AND THE PRODUCTION OF ILLICT DRUGS

(75) Inventors: Tim Bickett, Ridgway, IL (US); Frank Eiter, Morganfield, KY (US)

(73) Assignee: GloTell Products, Inc., Shawneetown, IL (US)

( * ) Notice: Subject to any disclaimer, the term of this patent is extended or adjusted under 35 U.S.C. 154(b) by 6 days.

(21) Appl. No.: 10/909,701

(22) Filed: Aug. 2, 2004

(65) Prior Publication Data

US 2005/0026298 A1    Feb. 3, 2005

Related U.S. Application Data

(60) Provisional application No. 60/567,740, filed on May 3, 2004, provisional application No. 60/492,663, filed on Aug. 5, 2003, provisional application No. 60/491,779, filed on Aug. 1, 2003.

(51) Int. Cl.
*G01N 37/00* (2006.01)
*G01N 31/22* (2006.01)
*G01N 33/15* (2006.01)
*G01N 21/29* (2006.01)
*G01N 21/64* (2006.01)
*G01N 33/22* (2006.01)
*C09K 11/06* (2006.01)

(52) U.S. Cl. .................. 436/56; 252/193; 252/301.19; 252/301.32; 252/364; 252/964; 252/965; 436/1; 436/2; 436/3; 436/4; 436/5; 436/111; 436/112; 436/113; 436/166; 436/172

(58) Field of Classification Search ................ 436/1–5, 436/56, 110–113, 164, 166, 172; 252/193, 252/301.19, 301.32, 364, 964–965
See application file for complete search history.

(56) References Cited

U.S. PATENT DOCUMENTS

| 1,915,965 | A | * | 6/1933 | Williams ..................... 436/3 |
| 2,062,435 | A | * | 12/1936 | Weiland ..................... 116/206 |
| 3,297,585 | A | * | 1/1967 | Hayden ................. 252/301.16 |
| 3,365,404 | A | * | 1/1968 | Bailey, Jr. et al. ........ 528/413 |
| 3,367,946 | A | * | 2/1968 | Stryker ....................... 549/227 |
| 3,609,179 | A | * | 9/1971 | Cavalla et al. .............. 560/37 |

(Continued)

FOREIGN PATENT DOCUMENTS

DE              3815605            * 10/1988

(Continued)

OTHER PUBLICATIONS

Adams, F. H. et al, Journal of the American Chemical Society 1932, 54, 4753-4754.*

(Continued)

*Primary Examiner*—Arlen Soderquist
(74) *Attorney, Agent, or Firm*—Lewis, Rice & Fingersh, L.C.

(57) ABSTRACT

Systems and methods providing for the introduction of a dye, particularly a xanthene dye, and more particularly a rhodamine dye, to liquid anhydrous ammonia to discourage theft of the anhydrous ammonia and provide for leak detection in storage vessels. The dye will stain objects which come into contact with the liquid anhydrous ammonia allowing for the detection of such contact. Generally, the staining will be visible to the naked eye, but may also fluoresce when exposed to a particular light source such as ultra violet (UV) light.

38 Claims, 3 Drawing Sheets
(2 of 3 Drawing Sheet(s) Filed in Color)

U.S. PATENT DOCUMENTS

| | | | | |
|---|---|---|---|---|
| 3,666,398 | A | * | 5/1972 | Tratnyek ........................ 8/619 |
| 3,772,099 | A | * | 11/1973 | Ryan et al. .................... 149/18 |
| 3,960,755 | A | * | 6/1976 | Beachem et al. ...... 252/301.16 |
| 4,226,194 | A | * | 10/1980 | Grahn ......................... 109/25 |
| 4,249,412 | A | | 2/1981 | Townsend, III |
| 4,272,298 | A | * | 6/1981 | Babler ........................ 106/496 |
| 4,326,981 | A | | 4/1982 | Molina |
| 4,379,144 | A | * | 4/1983 | Dilday ........................ 514/361 |
| 4,523,460 | A | * | 6/1985 | Strickler et al. .............. 73/200 |
| 4,758,366 | A | | 7/1988 | Parekh |
| 4,762,868 | A | | 8/1988 | Wright |
| 4,933,471 | A | * | 6/1990 | Lee ............................. 549/33 |
| 5,063,149 | A | * | 11/1991 | Suckling et al. ............... 435/4 |
| 5,149,138 | A | * | 9/1992 | Zemsky ....................... 283/70 |
| 5,149,453 | A | | 9/1992 | Parekh |
| 5,187,282 | A | * | 2/1993 | Carlier et al. ............... 548/455 |
| 5,244,813 | A | | 9/1993 | Walt et al. |
| 5,302,731 | A | * | 4/1994 | Pitner et al. ................. 549/394 |
| 5,304,493 | A | | 4/1994 | Nowak |
| 5,331,097 | A | | 7/1994 | Gunnell et al. |
| 5,421,192 | A | * | 6/1995 | Henry ........................ 73/40.7 |
| 5,623,080 | A | | 4/1997 | Neckers et al. |
| 5,677,187 | A | * | 10/1997 | Anderson et al. ............. 436/27 |
| 5,710,046 | A | | 1/1998 | Rutledge et al. |
| 5,723,338 | A | | 3/1998 | Rutledge et al. |
| 5,783,110 | A | | 7/1998 | Verdicchio et al. |
| 5,843,783 | A | | 12/1998 | Rutledge et al. |
| 5,928,954 | A | | 7/1999 | Rutledge et al. |
| 5,951,909 | A | | 9/1999 | Verdicchio et al. |
| 6,044,670 | A | * | 4/2000 | Citurs et al. ................... 70/169 |
| 6,165,384 | A | | 12/2000 | Cooper et al. |
| 6,170,320 | B1 | | 1/2001 | Scaringe et al. |
| 6,255,118 | B1 | | 7/2001 | Alfano et al. |
| 6,274,381 | B1 | | 8/2001 | Pauls et al. |
| 6,327,897 | B1 | | 12/2001 | Scaringe et al. |
| 6,452,020 | B1 | | 9/2002 | Batlaw et al. |
| 6,503,309 | B1 | | 1/2003 | Batlaw et al. |
| 6,582,730 | B1 | | 6/2003 | Goswami et al. |
| 6,603,020 | B1 | | 8/2003 | Moretti et al. |
| 6,605,731 | B1 | | 8/2003 | Batlaw et al. |
| 6,642,408 | B1 | | 11/2003 | Batlaw et al. |
| 6,645,391 | B1 | | 11/2003 | Greiner et al. |
| 6,689,391 | B1 | | 2/2004 | Goswami et al. |
| 6,800,358 | B1 | | 10/2004 | Batlaw et al. |
| 2004/0049079 | A1 | | 3/2004 | Murray et al. |

FOREIGN PATENT DOCUMENTS

| | | | |
|---|---|---|---|
| DE | 4315816 | * | 12/1994 |
| GB | 665478 | * | 1/1952 |
| JP | 4-312570 | * | 11/1992 |
| WO | WO 02/090316 A1 | | 11/2002 |

OTHER PUBLICATIONS

Glattfeld, J. W. E. et al, Journal of the American Chemical Society 1936, 58, 898-901.*

Corwin, A. H. et al, Journal of the American Chemical Society 1951, 73, 1184-1186.*

Kolling, O. W. et al, Analytical Chemistry 1959, 31, 1876-1879.*

Kolling, O. W. et al, Analytical Chemistry 1962, 34, 1653-1655.*

Takemoto, J. H. et al, Journal of the American Chemical Society 1969, 91, 3785-3788.*

Jolly, W. L. et al, Journal of Inorganic and Nuclear Chemistry 1971, 33, 783-789.*

Starobinets, G. L. et al, Chemical Abstracts 1975, 86, abstract 83123.*

Meyer, J. H. et al, Joint Conference Sens. Environ. Pollut.ion [Conf. Proc.], 4th (1978), Meeting Date 1977, 618-23 Publisher: ACS, Washington, D. C.*

Breant, M et al, Chemical Abstracts 1979, 90, abstract 197023.*

Asmus, E. et al, Chemical Abstracts 1979, 91, abstract 203811.*

Anastassiou, A. G. et al, Angewandte Chemie International Edition 1980, 19, 43-44.*

Aldrich Catalog 1988, pp. 34, 389-390, 476, 561, 669-670, 676, 711, 746-747, 1015, 1220, 1299, 1313-1314, 1317, 1370, 1538 and 1541.*

Brandsma, L. Recueil des Travaux Chimiques des Pays-Bas 1995, 114, 35.*

Fleming M. 2000, 4 pages web article (http://www.process-cooling.com/CDA/ArticleInformation/features/BNP_Features_Item/0,3674,15031,00.html).*

Zhou, S. et al, Analytical Chemistry 2002, 74, 4885-4888.*

Techniques of Water-Resources Investigations of the Untited States Geological Survey, Chapter A12, Fluorometric Procedures for Dye Tracing by James F. Wilson, Jr., Ernest D. Cobb and Frederick A. Kilpatrick, Revised 1986.

Reduction by Dissolving Metals. Part II,Journal of the Chemical Society, p. 809-813, 1945, by Arthur J. Birch.

Evaluating Insecticides for th Control of Narcissus Flies under Field conditions in Israel, D. Ben-Yakir, et al. (1997) Phytoparasitica 25(2):93-97.

* cited by examiner

DYE SOLUTIONS FOR USE IN METHODS TO DETECT THE PRIOR EVAPORATION OF ANHYDROUS AMMONIA AND THE PRODUCTION OF ILLICT DRUGS

CROSS REFERENCE TO RELATED APPLICATION(S)

This application claims priority to U.S. Provisional Application Ser. No. 60/491,779 filed Aug. 1, 2003, U.S. Provisional Application Ser. No. 60/492,663 filed Aug. 5, 2003, and U.S. Provisional Application Ser. No. 60/567,740 filed May 3, 2004. The entire disclosure of all the above documents is herein incorporated by reference.

BACKGROUND OF THE INVENTION (1) Field of the Invention

The present invention pertains to additives to anhydrous ammonia as well as systems and methods for using additives to anhydrous ammonia to detect the prior evaporation of anhydrous ammonia. This detection can indicate leaks in anhydrous ammonia storage vessels and can detect and inhibit the illegal production of methamphetamine.

(2) Background of the Invention

The use and production of methamphetamine is an illegal activity which impacts many aspects of American society. Known on the streets as "speed," "meth," "chalk," "ice," "crystal," "crank," or "glass," methamphetamine has become a substantial drug problem in much of the United States in both rural and urban areas. While methamphetamine use was traditionally associated with white, male, blue-collar workers, the drug is seeing increasing use amongst teens and other young adults. In a national survey conducted in the year 2000, an estimated 8.8 million people or 4 percent of the population of the United States were believed to have tried methamphetamine.

The drug, which is a powerful stimulant formed from ephedrine or pseudoephedrine, is recognized as causing a powerful stimulant rush, as well as a pleasurable high of relatively short duration. The high is believed to be caused by the release of very high levels of dopamine in the brain spurred by the drug. Physically, the drug is generally in the form of either a white odorless crystalline powder or a clear crystal. The drug dissolves easily in alcohol and water and can be taken through virtually any means including injection, inhalation, ingestion, and smoking.

While users of methamphetamine are generally pursuing a desirable high, methamphetamine use also has negative toxic effects on the body. A single dose can damage nerve terminals in the brain. High doses can also elevate body temperature to dangerous, sometimes lethal, levels, as well as cause convulsions. The drug can be addictive with addicts foregoing sleep and food in pursuit of a high. This addictive behavior can also lead to an increase in criminal behavior for the addict to obtain the resources to support the addiction. Chronic abuse can also directly lead to psychotic behavior including intense paranoia, visual and auditory hallucinations, and out-of-control rages that can be coupled with extremely violent behavior. Longer term damage can also include hardening of the brain arteries, mini-strokes and mental disabilities, as well as deterioration of bodily organs.

The production of methamphetamine is also a significant problem for the American public. The production itself is very hazardous involving numerous volatile chemicals such as lighter fluid, ammonia, chlorine gas, and others at production "labs" within homes, vehicles, abandoned buildings and rural structures. These labs regularly explode or catch fire causing property damage and the potential for injury or death. Even if law enforcement officials have reason to suspect a person or location is involved in methamphetamine production, they still may have trouble locating a lab or proving a connection as materials may be disposed of or hidden leaving little, if any, trace of the prior production.

Further, a high percentage of methamphetamine production is carried out by individual users for their own personal use and is performed in small labs. Dealers or those manufacturing large quantities of methamphetamine are generally more sophisticated and will often set up labs in more isolated rural areas far from others where an explosion may cause environmental damage and kill the producer, but often will not affect others unless they accidentally stumble on the lab while exploring the wilderness. Personal labs, however, can actually be more dangerous because they are often located in houses, apartments, garages, or even places of business and an explosion or fire from the lab can lead to a potentially dangerous situation placing not the only the users and their families at risk, but neighbors and emergency personnel who respond. Further, many teenagers or those experimenting in the chemistry of methamphetamine may not realize the danger of some of the underlying ingredients which can also lead to a hazardous situation.

Many of the chemicals used in the production of methamphetamine are now subject to consumer controls on their purchase as a means to disrupt production. Because of this, raw materials are often stolen from legitimate purchasers or manufacturers. One of the materials used to produce methamphetamine using a chemical procedure popular in illegal production is anhydrous ammonia, a clear liquid which boils (becoming ammonia gas) at −28° F. without leaving a trace. Anhydrous ammonia is regularly used by farmers as fertilizer being injected into the fields in a pressurized liquid form to improve agricultural production. As many farmers and fertilizer dealers therefore need to store and own large amounts of anhydrous ammonia for this use, farms, as well as fertilizer dealers, anhydrous ammonia transporters, and anhydrous ammonia refiners, have become targets of those who wish to steal the chemical for the production of methamphetamine.

In addition to the economic impact of such theft, farmers, fertilizer dealers, transporters, law enforcement and emergency responders may also be injured or killed by those attempting to obtain or use the chemical who are desperate not to get caught with the chemical (as punishments are often quite severe). Further, the theft can have environmental impacts as often once the thieves have what they want, they simply allow the remaining anhydrous ammonia in a storage tank to evaporate into the atmosphere resulting either from their failure to close a valve or from damage done to the tank during their theft resulting in a leak. Skin contact with anhydrous ammonia can cause rapid tissue damage and inhalation of ammonia gas can lead to major lung damage and death. Therefore, openly discharging tanks resulting from a completed theft can present a major problem to those persons nearby the tanks. Further, the liquid ammonia generally is not transferred by the thief in containers designed to store anhydrous ammonia. These improper containers can rupture explosively or leak. Sometimes simply more anhydrous ammonia than is needed is stolen. Then evaporation may be allowed to occur during transport to dispose of the excess.

Because of the chemical and physical properties of methamphetamine and the materials used in methamphetamine production, it is often difficult to detect when an individual is either using the drug, or producing the drug, unless they are either caught in production, caught with a functioning lab (or clear indications of a lab), or in a currently high state. As production and use are often performed in secret or with those who will not inform law enforcement, it can often be difficult to detect a person engaged in the drug's production or use during routine law enforcement activities. Instead, discovery can often require the use of searches which can violate Constitutional rights unless law enforcement has obtained an appropriate warrant. Law enforcement may, however, not be able to obtain the needed warrant without having already conducted the prohibited search.

In addition, production of one pound of methamphetamine produces about six pounds of toxic wastes. Lab sites are inundated with these toxic wastes and toxic wastes are often camouflaged, hidden, or buried to try and prevent their detection. Cleanup costs for each lab are thousands of dollars and often locating all the wastes in order to clean them up can be an arduous task. In rural areas, these toxic wastes often contaminate the soil and water, posing risks to innocent persons who stumble into these clandestine labs and also to the environment as a whole.

An industrial product related to anhydrous ammonia is ammonium nitrate. Each of these chemicals can be made from the other. Ammonium nitrate is also used as a fertilizer and has caused its own problems for law enforcement, particularly since it has been used as a raw material for use in production of explosives. In recent years, ammonium nitrate gained notoriety as a raw material for explosives when it was used to perpetrate a terrorist act against the United States. Further, methamphetamine producers have recently discovered that the material can be refined in their own production into ammonia suitable for their needs.

When examining the methamphetamine culture and its production as discussed above, a pervasive element should become clear: those who produce methamphetamine fear being discovered. Labs are kept on private property (or in remote areas) where searches by law enforcement are difficult to conduct and may be unlikely to find the necessary evidence to carry out an arrest. Further, the acts related to obtaining the raw materials are often conducted clandestinely using theft and third parties to carry out legitimate smaller purchases to fund a thriving underground market in the necessary supplies. Further, methamphetamine labs use numerous products which have other legitimate uses for which a vast percentage of the purchasers utilize them. As the raw materials used to produce methamphetamine are often indistinguishable from those used legitimately, detection of methamphetamine production even after the fact can also be difficult.

SUMMARY OF THE INVENTION

Because of these and other problems in the art, described herein are systems, compositions, and methods for helping to provide indications of when individuals, buildings, vehicles, containers, and other objects, have been around or in contact with either methamphetamine or chemicals used in its production, particularly anhydrous ammonia. These systems, compositions and methods preclude the need for invasive searches and can preferably be useful long after the time when any evidence of using or producing the drug otherwise would be observable.

In an embodiment, the invention provides a method of detecting the prior presence of liquid-state ammonia including the steps of introducing into liquid-state ammonia a xanthene dye, the dye creating a stain on a material in contact with the liquid-state ammonia upon the conversion of some of the liquid-state ammonia from a liquid to a gas; and detecting the stain. In various alternate embodiments this method provides a xanthene dye that is a fluorene, a fluorone, a pyronin, a rhodamine, is rhodamine WT, is fluorescein, or is a dye identified within the range of indices, 45000–46999, of the COLOUR INDEX, volume 5, Chemical Classifications, 1976. In an embodiment, the step of detecting the prior presence of liquid-state ammonia is performed through detection by an unaided human eye. In alternate embodiments, the stain is colored under visible light illumination, or fluoresces in response to illumination by ultraviolet (UV) light. In an embodiment of this method, the xanthene dye comprises between about 1 to 100 parts per million of ammonia on a weight to weight basis.

In a further embodiment, the invention provides a method of detecting the production of a controlled substance including the steps of providing a solution of a xanthene dye in a solvent used in the production of the controlled substance, using the solution in the production of the controlled substance, thereby generating production byproducts that comprise the solution, staining materials contacted by one of the solution, the byproducts, and the controlled substance, and detecting the staining on the materials, this detection being possible even in the absence of any or all of the solution, the byproducts, and the controlled substance. In various alternate embodiments this method provides a xanthene dye that is a fluorene, a fluorone, a pyronin, a rhodamine, is rhodamine WT, is fluorescein, or is a dye identified within the range of indices, 45000–46999, of the COLOUR INDEX, volume 5, Chemical Classifications, 1976. In an embodiment, the step of detecting the prior presence of liquid-state ammonia is performed through detection by an unaided human eye. In alternate embodiments, the stain is colored under visible light illumination, or fluoresces in response to illumination by ultraviolet (UV) light. In an embodiment of this method, the xanthene dye comprises between about 1 to 100 parts per million of ammonia on a weight to weight basis. In further alternate embodiments the method of detecting the production of a controlled substance can be preformed when the controlled substance is methamphetamine, as well as when the solvent is ammonia.

In a still further embodiment, the method of detecting the production of a controlled substance includes the step of having the xanthene dye survive the production of the controlled substance, thereby staining the controlled substance. In an embodiment of this method with the additional step of having the dye survive the production of the controlled substance, the method can be preformed when the controlled substance is methamphetamine, and additionally when the xanthene dye resides on the surface of the methamphetamine. In alternate embodiments of this method when the controlled substance is methamphetamine, the xanthene dye cannot be washed from the surface of the methamphetamine with water, acetone, toluene, petroleum ether or xylenes, or the xanthene dye stains materials which come into contact with the methamphetamine. In an embodiment, the staining of the methamphetamine comprises staining visible to the naked eye. In alternate embodiments, the staining of the methamphetamine is colored under visible light illumination, or fluoresces in response to illumination by ultraviolet (UV) light.

In an embodiment, the present invention is a solution for detecting the prior presence of liquid-state ammonia comprising liquid anhydrous ammonia and a rhodamine dye dissolved in the liquid anhydrous ammonia to form an ammonia solution. In such an embodiment, the rhodamine dye will leave a stain on materials which were in contact with the ammonia solution upon conversion of some of the ammonia to a gas. In an embodiment of the solution, the stain is a predetermined color visible to the human eye under illumination by visible light. In an alternate embodiment, the solution is not the predetermined color.

In an embodiment, the present invention is a method of enabling the detection of the prior presence of liquid-state ammonia including the steps of introducing a dye into liquid-state ammonia to create a blend, the dye creating a stain on materials in contact with the blend upon the conversion of the ammonia from a liquid to a gas, and storing the ammonia and dye in a pressurized tank.

In an embodiment, the present invention is a method for deterring the theft of liquid-state ammonia including the steps of providing liquid-state ammonia, adding a dye to the liquid-state ammonia; and forming a solution of the ammonia and the dye, the solution generating a stain on objects that contact the solution. In such an embodiment, the step of forming a solution includes forming a homogeneous mixture.

In alternate embodiments, the stain is only detectable upon evaporation of the ammonia from the solution, the solution is visibly distinct from the liquid-state ammonia, the liquid-state ammonia comprises anhydrous ammonia, and the dye comprises one of a colored dye, a fluorescing dye, a xanthene dye, a rhodamine dye. In an embodiment wherein the liquid-state ammonia comprises anhydrous ammonia, the anhydrous ammonia is stored under pressure.

In an embodiment, the present invention is a method of deterring the theft of anhydrous ammonia including the steps of providing a sealed container of anhydrous ammonia, and affixing a label to the sealed container, the label indicating that the anhydrous ammonia includes a dye that will leave a detectable stain on objects that contact the anhydrous ammonia but which is not readily visible in the anhydrous ammonia, but wherein the anhydrous ammonia does not include the indicated dye. In an alternate embodiment, the label indicates that the anhydrous ammonia includes a dye that will stain a controlled substance produced using the anhydrous ammonia.

In an embodiment, the present invention is a method of inhibiting the use of a controlled substance including the steps of providing a solution of a dye in a solvent used in the production of the controlled substance, using the solution in the production of the controlled substance, having the production stain the controlled substance, and inhibiting use of the controlled substance due to a decreased desire to use the controlled substance when stained as compared to the controlled substance absent the stain. In an embodiment, the stained controlled substance is able to stain materials contacted by the stained controlled substance. In a further embodiment these materials include human skin.

In an embodiment, the present invention is a method of detecting the prior presence of ammonium nitrate including the steps of introducing onto the surface of ammonium nitrate a xanthene dye, staining materials contacted by the ammonium nitrate, and detecting the stain. In a further embodiment, the dye remains in ammonia produced from the ammonium nitrate. In various alternate embodiments this method provides a xanthene dye that is a fluorene, a fluorone, a pyronin, a rhodamine, is rhodamine WT, is fluorescein, or is a dye identified within the range of indices, 45000–46999, of the COLOUR INDEX, volume 5, Chemical Classifications, 1976. In an embodiment, the step of detecting the prior presence of ammonium nitrate is performed through detection by an unaided human eye. In alternate embodiments, the stain is colored under visible light illumination, or fluoresces in response to illumination by ultraviolet (UV) light.

BRIEF DESCRIPTION OF THE DRAWINGS

The patent or application file contains at least one drawing executed in color. Copies of this patent or patent application publication with color drawing(s) will be provided by the office upon request and payment of the necessary fee.

DETAILED DESCRIPTION OF THE PREFERRED EMBODIMENT(S)

Discussed herein are systems and methods, as well as dyes, which can be used with liquid anhydrous ammonia or other ammonia products or precursors, which provide for the detection of the conversion of liquid ammonia to gaseous ammonia. In this application the term ammonia will generally refer to compositions that are primarily ammonia ($NH_3$), particularly as distinct from a solution of ammonia in water, which is commonly referred to as ammonia. In this application a solution of ammonia in water or any other liquid will be identified as such a solution. The use of the term ammonia herein encompasses anhydrous ammonia, particularly liquid anhydrous ammonia, including the industrial product produced and sold in a commercial grade on a bulk scale for numerous applications, particularly as an agricultural fertilizer. Commercial grade anhydrous ammonia typically has a water content of less than 0.5%, with water being the greatest impurity, and the ammonia otherwise being greater than 99.5% pure. The term liquid ammonia as used in this application refers to ammonia in the liquid state, otherwise termed liquid-state ammonia.

Liquid and gaseous ammonia are generally clear and colorless with the gas having a characteristically pungent smell. Ammonia has a boiling point of −28° F. and a freezing point of −107.9° F. This means that at ordinary indoor and outdoor temperatures ammonia is a gas. In commercial applications, however, ammonia is typically stored and transported in specialized containers under pressure, so that even at normal temperatures it can be maintained as a liquid. Once the pressure is released, if the temperature is greater than −28° F., liquid ammonia will boil. After the boiling or evaporation of liquid ammonia from a surface and the dissipation of the resulting gas, the prior presence of the ammonia will generally not be detectable.

In general, there are discussed herein marker or tracer dyes which can be placed into liquid ammonia, or precursors or products of ammonia, such as, but not limited to ammonium nitrate, that provide for staining of surfaces and other materials which come into contact with the liquid ammonia, or ammonia precursor or product. As used herein the term dye encompasses compositions more commonly referred to generally as colorants or pigments. Concerning liquid ammonia, it is generally preferred that this staining become apparent after the evaporation or boiling of liquid ammonia, which converts the liquid to a gas. Further regarding liquid ammonia, it should be recognized that the staining caused by the compositions, systems, and methods discussed herein is particularly useful in the detection of at least two events. A first event is the unintended release of liquid ammonia due to tank leaks or similar problems in legitimate and legal uses of ammonia. A second event is the illegal acquisition and use of liquid anhydrous ammonia, particularly in the production of methamphetamine.

Anhydrous ammonia is highly corrosive, and therefore toxic. Legitimate users will generally try to avoid exposure to the liquid and gas to prevent danger to themselves, others, and the environment. For safety reasons, having an indication that ammonia evaporation or boiling is occurring or has previously occurred serves the purpose of detecting an unintended release that needs to be remedied. Further, indications of an unintended leak in a legitimate use can provide information of a potential danger to emergency responders and enable a successful evacuation of an area if necessary. As the tanks used to store anhydrous ammonia are often converted to use for storage of propane, similar situations may arise with respect to unintended leaks of propane from such tanks. In these situations, as with ammonia, a dye placed into the propane can be similarly beneficial.

Detection of the evaporation or boiling of liquid ammonia in the second event, illegal acquisition or use of ammonia, will generally occur because those persons illegally acquiring or using ammonia, typically methamphetamine producers, generally lack the necessary sophisticated liquid anhydrous ammonia handling equipment or lack the skill or patience to use it properly. Thieves, methamphetamine producers, and conspirators therewith are likely to be exposed to evaporating or boiling ammonia as the ammonia is released from a pressurized storage container during transfer to a thief's container, and during other uses of the ammonia by a thief or a conspirator or a methamphetamine producer, such as in the synthesis of methamphetamine. Detection of such an illegal event will generally be possible because dye stains remaining after ammonia boiling or evaporation will occur on objects and in locations where it is improbable that the ammonia was being used legitimately.

In a first embodiment, the compositions, systems, and methods relate to chemicals, specifically dyes, which may be placed in ammonia or can be added to (such as by surface spraying) ammonia precursors or products (such as solid ammonium nitrate) and which are non-volatile, such that the dyes will remain on contacted surfaces during boiling, evaporation, or sublimation of ammonia, its precursors, or products, and will stain those surfaces. It is preferable that the dye stain the objects present during, and the products of, the production, transportation, containment, or use of ammonia where such steps result in uncontrolled boiling or evaporation of ammonia.

While a plethora of dyes may be used in detecting the evaporation or boiling of liquid ammonia, it is preferred that the dye have certain characteristics. The dye is preferably soluble in liquid ammonia. The dye preferably does not react with ammonia in a way that degrades the dye, or at least its ability to stain. The dye preferably will stain non-porous, porous, or semi-porous substances, particularly those used for storage of ammonia and those used in the production of methamphetamine (for instance, plastics, paper, human skin, and clothing), as well as those substances likely to be in the environment of a methamphetamine production lab, such as wallpaper, carpet, cement, dry wall, and wood. The dye will also preferably be relatively easy to remove from the skin and other washable surfaces to an extent that it cannot be easily detected by unaided sight, since the absence of such washability may impede lawful uses of anhydrous ammonia. A preferred dye will be relatively difficult to remove from such materials and surfaces, however, to levels below the detection limit of other non-invasive detection methods. The preferred dye will also be generally safe with respect to human and animal health, including to exposures such as ingestion and skin contact, and with respect to the environment generally. That is, a preferred dye can be safely placed into soil when an anhydrous ammonia solution of dye is used as fertilizer. It is further preferred that the dye be sufficiently stable so as to be maintained at operative concentrations in liquid ammonia at all times prior to evaporation of the ammonia. That is, in a preferred embodiment, the dye can be maintained in liquid ammonia in all forms of storage and transportation devices, including those that are improvised and used for illegal purposes (including modified propane tanks and food grade thermoses and coolers), until evaporation of the anhydrous ammonia occurs. Additionally, for reasons discussed further below, the preferred dye will be difficult to remove from ammonia either before or during the production of methamphetamine, thus, allowing the dye to carry into the final methamphetamine product. Xanthene dyes, particularly rhodamines, have most of these preferred properties.

In an embodiment, it is further preferred that the dye is stable to or generated or regenerated during the process of converting ammonium nitrate to ammonia, such that the dye could be placed on solid ammonium nitrate, and remain in any liquid ammonia or ammonia gas derived from that ammonium nitrate. In such an embodiment, when the dye is placed with ammonia nitrate, the dye may also stain objects which come into contact with the solid ammonium nitrate.

In a preferred embodiment, the dye selected is a xanthene dye such as a fluorene or flourone. The class of xanthene dyes is a well known class of dyes containing a xanthene backbone, as shown below in structure (1), which may be substituted at numerous positions, replacing the indicated hydrogen atoms with one or more substituents that may be simple (such as an atomic moiety) or complex (such as a molecular moiety). According to the Society of Dyers and Colourists and the American Association of Textile Chemists and Colorists, as published in their work, COLOUR INDEX, volume 5, Chemical Classifications, 1976, the entire disclosure of which is herein incorporated by reference, the xanthene dye class is covered by colour indices 45000–46999. While the COLOUR INDEX is not exhaustive in listing xanthene dyes, or any other dyes in any other class, it provides a general reference for industrially significant dyes in the various classes and thereby also provides a source for class definitions.

(1)

The selected dye is more preferably a pyronian, and still more preferably a rhodamine. In alternate embodiments, the dye is rhodamine WT (2) (also known as Acid Red 388) or fluorescein (3) (also known as Acid Yellow 73). Both of these dyes are commonly used as fluorometric tracing dyes, particularly in waterways, are considered environmentally safe, and have strong fluorescent properties when exposed to ultraviolet (UV) light. It should be understood, however, that any xanthene dye could be used in alternative embodiments of the invention, especially those dyes capable of being dissolved into anhydrous ammonia in amounts of about 1 to 100 parts per million on a weight to weight basis (ppm w/w).

In further embodiments, other dyes used as fluorometric tracing dyes with strong fluorescent properties (including aminoketones such as Lissamine FF) could be used, as they will often have similar properties and operate in a similar way to xanthene dyes when placed in liquid ammonia. As well, other types of dyes, such as, but not limited to, vat dyes, fluorescent dyes, food dyes, clothing dyes, or hair dyes, particularly those which are hydrophilic, may be used. Inks, pigments, or other materials which provide coloration (encompassed herein within the definition of dye) can also be used in alternative embodiments, on their own or in conjunction with the other dyes discussed above. All of these dyes will result in indications of the presence or prior presence of liquid ammonia. Certain dyes, however, particularly xanthene dyes that contain no large halogen atoms, are preferred due to their fluorescent properties, resulting in detectablity even in minute quantities. Further, xanthene dyes such as rhodamines are generally not visible in the liquid ammonia under illumination by visible light, and only express coloration upon evaporation of the liquid ammonia.

While the dyes discussed above generally provide for visual detection when they stain contacted materials, either directly by coloring an object or indirectly such as through fluorescence, visual detection is by no means required. In other embodiments, the fluorescence emission is non-visible. In still further embodiments, dyes or tracers which emit, absorb, or reflect other signals such as x-rays, particles, infrared (IR) or ultraviolet (UV) emissions, audio signals, ultrasonic signals, or any other form of detectable signal, can alternatively or additionally be used to detect the presence or prior presence of ammonia, or a precursor or product thereof.

In an embodiment of the invention, the ammonia is "dyed," i.e., provided with the ability to leave behind a stain, by simply intermixing the xanthene dye into the liquid anhydrous ammonia. In a preferred embodiment, the intermixing results in the dissolution of the dye in the liquid ammonia, including when the intermixing is of a dye solution and liquid ammonia that results in the dye remaining in solution. As used herein, dissolution means the creation of a homogeneous mixture either by true solvation or by another physical mechanism such as the creation of a suspension. At or after dissolution, the liquid ammonia solution is then exposed to objects and materials that will be stained during the evaporation or boiling process. As the ammonia solution boils or evaporates, the staining effect of the dye remains on the surface from which the liquid ammonia departs. Through the remaining stain, the prior presence of liquid ammonia on that location is detectable.

In a preferred embodiment, the dye is added in such quantities to liquid ammonia that the dye is not visible or is only slightly visible to the human eye when the dye in ammonia solution is illuminated with light in the visible spectrum (about 400–800 nm). (Note that illumination by light in the visible spectrum is considered a normal lighting condition as this is provided by sunlight and white electric lights, for instance.) In an alternative embodiment, the liquid ammonia solution of the dye is obviously colored with a dye that is visible to the human eye under illumination by light in the visible spectrum. In either case, the solution of ammonia and dye can then be used as ammonia typically would be used under circumstances in which no dye was dissolved in the ammonia.

In further embodiments, the stain remaining after evaporation or boiling of the ammonia may be or may not be visible under visible light illumination, regardless of the coloration of the dye in ammonia solution. A generally non-visible stain generally eliminates inconvenience in lawful uses of ammonia resulting in staining. In either case, where the stain is only expressed upon evaporation or boiling, hoses, containers, and other devices used in containing ammonia and in which no boiling or evaporation is intended to occur are generally not stained. Where the stain is only expressed upon evaporation or boiling, the presence of the stain usually indicates an unintended or an unlawful release, which are the types of release generally of interest.

The amount of dye which is added to ammonia can, in many cases, be quite small and still produce the effects discussed above. It is generally preferred that the concentration be between about 1 and 100 ppm w/w of dye in liquid anhydrous ammonia. This concentration results in the dye comprising a quite small concentration in the soil for a typical fertilizer application. (In a typical fertilizer application, ammonia is applied at a rate of about one ton per eight acres. Assuming an even application depth of one foot, and a consistent soil density of 40 lbs per cu. ft., 13,939,200 lbs of soil are treated by a ton of ammonia. Assuming a 10 ppm w/w concentration of dye in ammonia, the soil concentration of dye is about 1.4 parts per billion on a weight to weight basis (ppb w/w).) These relatively small amounts of dye in ammonia can still result in impressive staining of materials as discussed in the Examples section and shown in the figures. In fact, small amounts of dye are often actually more effective at staining, particularly fluorescent staining, since as a result of self quenching, high concentrations of a fluorescent dye may have a reduced fluorescence compared to lower concentrations.

For the purposes of the rest of this discussion, it will be presumed that a rhodamine dye, particularly rhodamine WT, is used as the dye. One of ordinary skill in the art, however, would understand how the discussion below could be adapted for use with other dyes that are indicated above.

Rhodamine WT is a preferred dye because of its numerous properties useful for detecting the presence or prior presence of ammonia, or precursors or products thereof. Useful properties include that rhodamine WT is visibly colored a shade of red (under visible light illumination) as well as being fluorescent. Rhodamine WT has strong fluorescent properties, generating significant quantities of visible spectrum light of a red or pink color upon irradiation with ultraviolet light, even for small amounts of the dye. This fluorescent property makes likely the detection of a stain on various surfaces, even for small amounts of the dye, such as amounts that are possibly not even visible under normal visible light illumination. Additionally, the dye is non-volatile, so it will remain on the stained object under normal temperature and pressure conditions. A further useful property of rhodamine WT is that the liquid ammonia solution of the dye is not, itself, obviously colored red or pink. The dye in solution is not readily apparent under visible light illumination as it does not cause significant discoloration of the liquid ammonia, though a slight yellowing may be present. Still further, rhodamine WT is commonly used as a water tracing dye. It has been added to the environment by professionals in fairly concentrated form in the past and will continue so to be, thus indicating a determination as to the dye's fairly high safety level with respect to animal and environmental health. Still further, rhodamine WT embodies the preferred property that the dye be able to survive the production of methamphetamine so as to stain the resultant drug product. In this way, all facets of the drug's production, transport, and use pose a potential staining risk, which makes all of these activities more likely to be detected.

In an embodiment, the staining by an ammonia solution of rhodamine WT operates as follows. When the ammonia is converted from a liquid to a gaseous state (which certainly occurs at temperatures of −28° F. and above under normal pressures) the dye is left behind on the surface from which the ammonia boiled or evaporated because the dye is not volatile. In accord with rhodamine WT's natural properties (mentioned above) the stain generally is visible as a red stain under both visible and UV light irradiation. Thus, an ammonia solution of rhodamine WT will stain objects exposed to the solution or the vapor thereof (which vapor contains a mixture of both liquid droplets and gaseous ammonia) upon evaporation or boiling of the ammonia. Materials that may be stained in this way include, but are not limited to, papers, clothing, textiles, and human skin. The rhodamine WT stain will also fluoresce a pink or red color when exposed to ultraviolet light.

Figure 3:
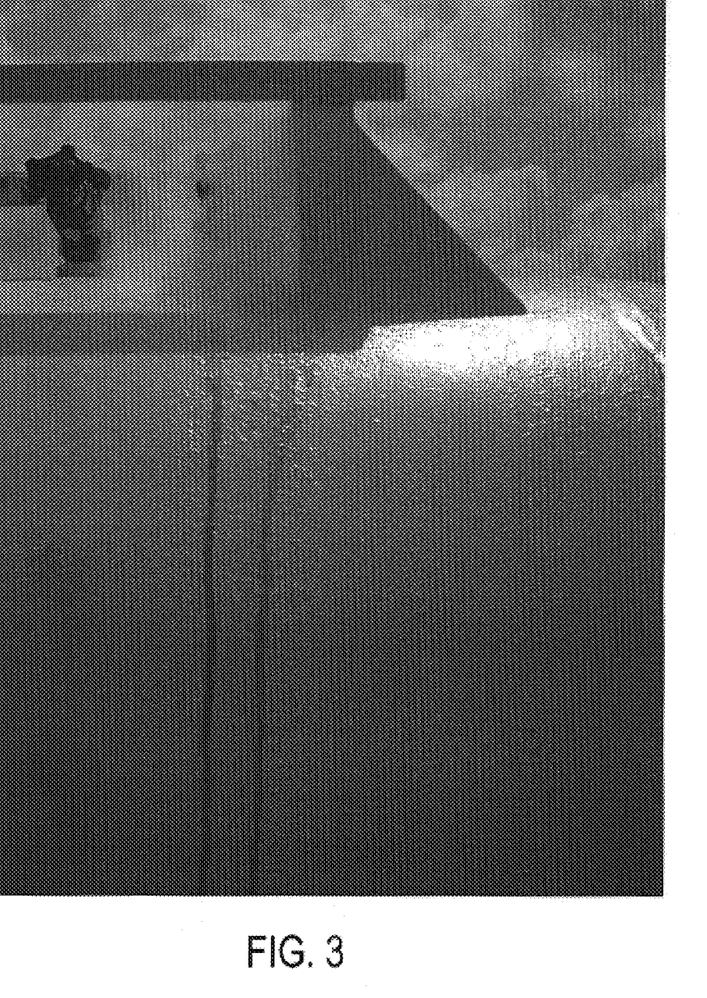
FIG. 3 shows a color photograph of a stain down the side of an anhydrous ammonia nurse tank. Anhydrous ammonia including a rhodamine dye is shown leaking at the top.

The staining effect of the solution of dye in ammonia, as discussed above, is particularly useful with regard to legitimate uses of ammonia, particularly as when a liquid anhydrous ammonia tank develops a leak. When such a leak occurs in a tank holding the dye and ammonia solution, the tank and nearby objects will rapidly become stained near the leak point as liquid or vapor will be forcibly ejected from the tank under pressure. In an embodiment, staining is visible to the naked eye under typical visible light irradiation, such as by the sun or normal white electric lights. Such visibility is particularly preferred as it provides an immediate indication of danger and allows for an emergency response to be initiated immediately if need be. The staining provides a quick indication that the tank needs to be repaired. Further, if a leak should occur in a pipe, tank, or any other structure being used legitimately, the user will have near immediate indication of the leak, and can shut down machinery or institute additional containment measures to prevent death or serious bodily or environmental injury. Such detection of unintentional releases is a particularly valuable benefit because the dye can remain in the liquid ammonia at all stages of production and use of the ammonia, so such detection is available throughout the stages of production, storage, and use. Note that the dye is not introduced into an empty tank to try to detect leaks, but rather is present when there is liquid ammonia in the tank (or other storage or transport device) and therefore can stain the tank if a leak develops at anytime there is liquid ammonia in the tank. This is the same time when a tank leak creates a danger to persons and the environment. FIG. 3 shows a picture of a leaking valve on an anhydrous ammonia nurse tank. The white cloud of ammonia gas is seen towards the top valve of the tank, but would clearly not be easily seen from a distance; the two streaks of pink, however, from a rhodamine WT dye, on the white surface of the tank are immediately apparent.

In addition to the general detection of the presence or prior presence of ammonia, as discussed above particularly with respect to detection of unintentional releases in legitimate uses, the inclusion of a dye in anhydrous ammonia can serve in many ways to help combat the major societal problems related to methamphetamine production and use. With respect to persons producing and using methamphetamine, and persons trafficking in ammonia for illegal purposes, the solution of dye in ammonia is a substantial aid in identifying these individuals. With respect to law enforcement and emergency responders who first appear on a scene where methamphetamine production activities have been taking place, the staining that results from a solution of dye in ammonia is a substantial aid in identifying the hazardous nature of the scene. With respect to taking steps broadly toward eradicating these societal problems, the solution of dye in ammonia is a substantial deterrent to both the production and use of methamphetamine. Further, as theft of anhydrous ammonia and leaks in storage tanks often go hand-in-hand, the detection of theft can also help prevent additional damage from a leak as a result of that theft.

The staining effect of the solution of dye in ammonia can facilitate the identification of producers and users of methamphetamine and conspirators therewith, both by direct and indirect methods. As discussed above, the dye in ammonia solution will stain materials and surfaces from which the ammonia evaporates. In this way anyone using or transporting the ammonia has the potential to be contacted, particularly on their skin or clothing, by ammonia and stained when it boils or evaporates. In an embodiment, the dye may also stain the end product methamphetamine, which may in turn stain the person selling the product or the person using the product when they come into contact with it. It is the stain on the skin of individuals involved with methamphetamine production and use that leads to their direct identification. For such a use, it is preferred in an embodiment that the staining be visual to the naked eye under typical visible light irradiation, such as by the sun or normal white electric lights. Such visibility allows for detection by a plethora of parties.

In an indirect sense, producers and users of methamphetamine and traffickers of ammonia will be identified through the staining effect of the solution of dye in ammonia on objects and materials other than skin. The staining effect can help identify the presence or prior presence of liquid ammonia and other products used in the illegal manufacture of methamphetamine in vehicles and buildings, and on containers and clothing, as well as other objects nearby. This staining will provide evidence to help in the identification and prosecution of those involved with methamphetamine since those persons who own or have a right to use or can otherwise be connected to the property that was stained will be implicated as potential wrongdoers. Depending on the nature of the detection, the presence of a stain may be sufficient grounds to justify a more invasive search, the arrest of a suspect, or confiscation of certain goods, such as for further testing.

For example, a routine traffic stop can allow law enforcement personnel to detect that the driver or occupants recently were exposed to anhydrous ammonia, possibly warranting a further search of the vehicle or potentially providing sufficient grounds to obtain a search warrant of a home. While a visibly colored stain would make such detection simple, where the stain was not visible, a fluorescent stain could be detected by shining an ultraviolet light on a suspect. Investigation by UV light is a non-invasive procedure that is performed with fairly common technology which may make such searches by police reasonable. Such searches may allow law enforcement on routine business to detect that an individual may have had recent contact with anhydrous ammonia, ammonium nitrate, or methamphetamine. Law enforcement may also shine UV lights on vehicles or on dwellings or other locations from a distance to perform other noninvasive searches.

In further examples, neighbors, landlords, garbage collectors, service personnel, school officials, club bouncers or anybody else having contact with an individual may see indications of the staining from a solution of dye in ammonia and contact law enforcement or take other action. In particular, night clubs occupy the convenient coincidence of locations where methamphetamine likely may be used and there is often a presence of UV lights for other legitimate uses. UV lights are typically used as a method to determine paying customers or customers over a particular age (such as the legal age for alcohol consumption) through their use in combination with a fluorescing chemical hand stamp or may be used for environmental light effects. Under circumstances of typical ultraviolet light use in these settings, a club owner or bouncer may detect that an individual may have been in contact with methamphetamine or involved in its production, either in the club or prior to entering the club, and can alert law enforcement or take other responsible measures. In all of these ways, both direct and indirect, the identification of those involved in methamphetamine production becomes more easily obtainable.

Just as for the situation where a hazardous ammonia leak is detected through staining in an unintentional release in a legitimate use of ammonia, where illegal uses and trafficking are involved, the indication of the presence or prior presence of ammonia at a site where it would otherwise not be expected is likely to indicate hazardous conditions, due for instance to the presence of liquid ammonia or to other chemicals and apparatuses related to methamphetamine production, all of which present multiple health hazards. Where the stain is not obvious under visible light illumination, but is fluorescent, UV lights can be used by cleanup crews or crime scene units to locate evidence and dispose of contaminated articles.

Figure 1:
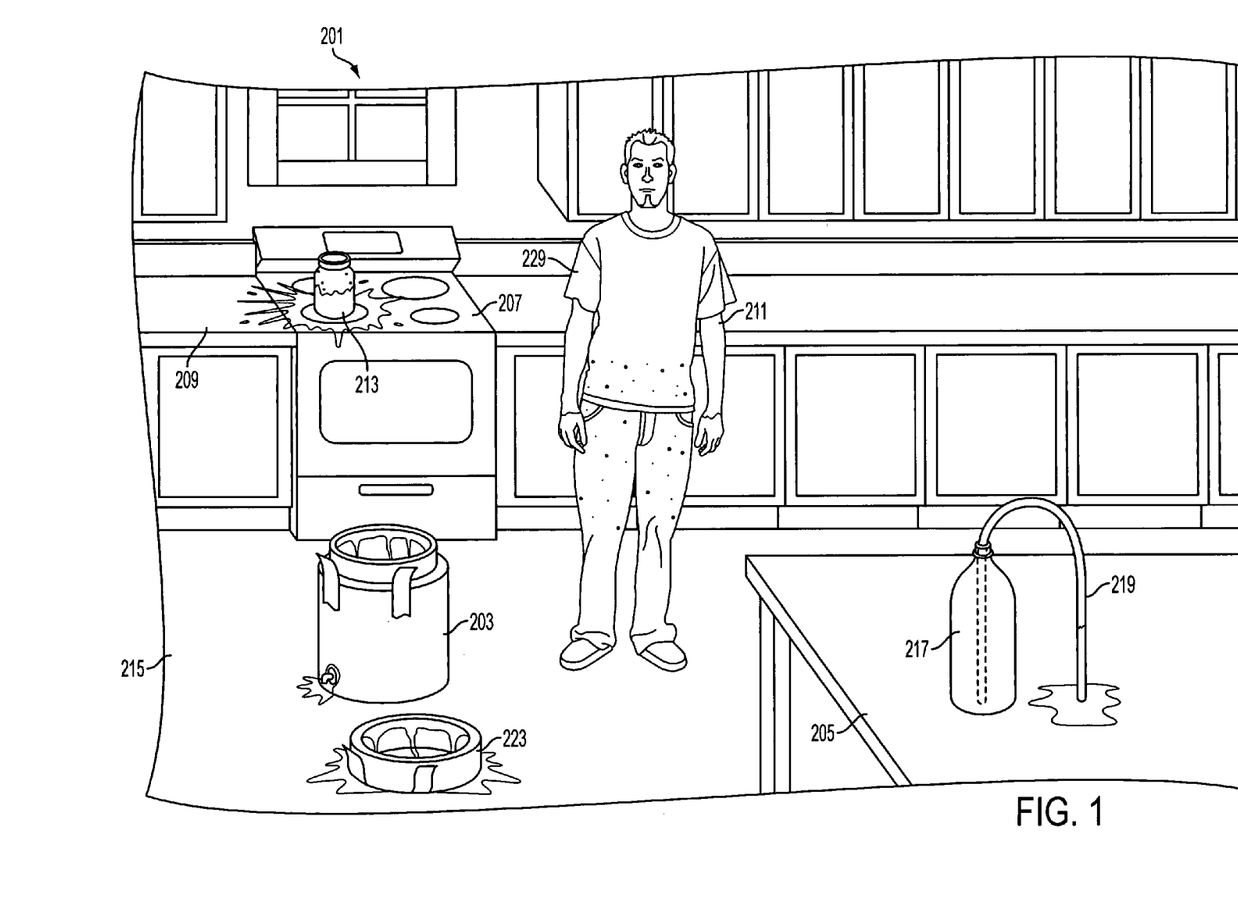
FIG. 1 shows an exemplary drawing of a household methamphetamine lab with indications of staining on various items resulting from an embodiment of the invention.

An indication of the staining properties of an embodiment of the present invention is shown in FIG. 1, where stains (265) are shown that would be an aid to both identifying individuals involved and identifying the hazardous nature of the location. In this exemplary embodiment, a solution of dye in ammonia was used in a clandestine methamphetamine lab (201) and has stained various items that were in contact with the liquid anhydrous ammonia which has since evaporated. The vessel (203) and the vessel's lid (213) used to transport the liquid ammonia and dye solution have been stained (265). Also as a result of a spill from or escaping vapor from the vessel (203), the floor (215) is stained (265). Escaping vapor or a spill has also stained (265) a user (211) of the dye in ammonia solution, as well as the user's clothes (229). Further, items used in the lab such as ajar (213) and the pipe (219) used in conjunction with a two-liter bottle (217) as part of the salting procedure are stained (265). Each of these also released vapor or liquid staining (265) the stove (207), counter (209) and table (205).

Because of all the above staining properties, the inclusion of a dye in liquid ammonia makes the production and use of methamphetamine a messier endeavor and one more likely to be detected. This messiness and increased detectability resulting from the solution of dye in the ammonia leads to significant deterrent effects on those who would otherwise be involved in methamphetamine production and use. The deterrent effects include psychological deterrence, physical deterrence, and economic deterrence.

The psychological deterrence comes from a decreased willingness to participate in activities related to methamphetamine production and use due to the desire not to be stained personally or have one's possessions stained and a distaste therefor, as well as an increased fear of being identified and prosecuted for these activities. Since the staining may come from either the dye in the ammonia solution itself during stealing, transportation, or use thereof, as well as from methamphetamine stained as a result of a production using a dye in ammonia solution, all persons involved in activities related to methamphetamine production and use may be deterred. To take advantage of this psychological deterrent effect, warning signs may be used to indicate that certain stored ammonia includes a tracer dye. Such warning signs may be used as a deterrent to illegal acquisition of the ammonia or dye in ammonia solution so labeled whether or not the dye is actually present in the ammonia in the container so labeled, and whether or not the dye is visible in ordinary illumination such as sunshine or white electric lights. The psychological deterrent effect may be present in any number of specific circumstances in which one decides not to make, use, transport, or otherwise be in contact with liquid ammonia, liquid ammonia including a dye, or a product such as a drug made therefrom.

A methamphetamine producer needs to engage in elaborate protection methods to prevent the dye from being readily apparent on themselves, and objects and materials that come into contact with a dye in ammonia solution, including their own personal and real property. Many methamphetamine producers will not or cannot take such precautions. Because the precautions to reduce the risk of staining from use of a dye in ammonia solution may be costly or time consuming or otherwise inconvenient, a person who would otherwise be a methamphetamine producer may decide not to produce methamphetamine or may produce the drug by alternative methods which may be less reliable, take more time, and produce an inferior product. This is an example of an embodiment of the deterrent effect on methamphetamine producers. In another embodiment, while not a complete deterrent, if a methamphetamine producer decides not to produce the drug in their residence for fear of detection by a landlord or someone else, and instead produces in a remote area with a low population density, an alternate benefit is obtained by the general deterrent effect of staining, which is greater safety for neighbors near the location of the producer's residence, and potentially greater safety for emergency responders, who face a less confined hazardous site when the remote production lab is discovered.

Figure 2:
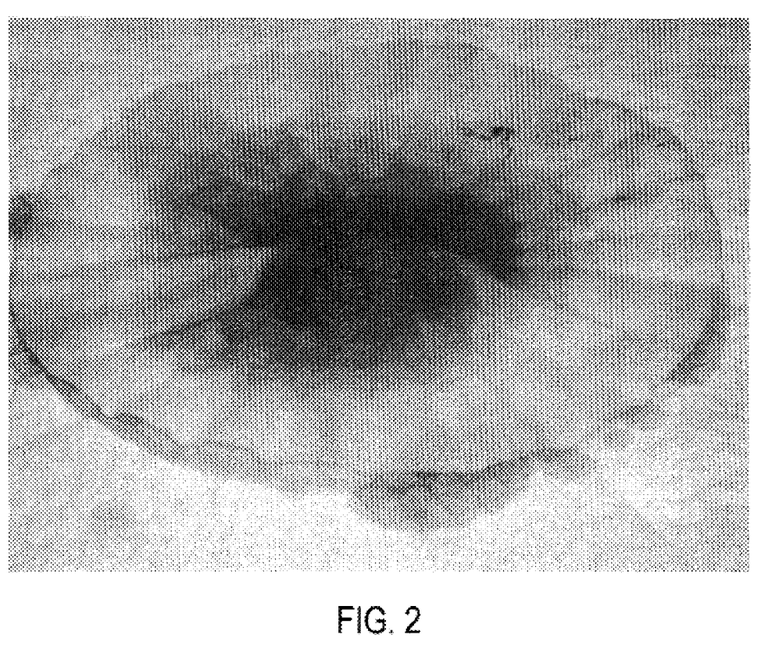
FIG. 2 shows a color photograph of a coffee filter including methamphetamine stained pink from being produced using anhydrous ammonia including a rhodamine dye.

Further, because in an embodiment the methamphetamine product is stained, it is readily apparent to a potential user that the tracer dye could be transferred to them through use of the methamphetamine produced using the dyed anhydrous ammonia. FIG. 2 provides a coffee filter including stained end-product methamphetamine. Such staining capability may deter purchase or use of the stained methamphetamine. In an example, a teenager at a party may be willing to try unstained methamphetamine with the expectation that by the time they return home all evidence of their use will have disappeared, but that same teenager likely will be much less willing to try the same drug when, for instance, use of it would be easily detected by their parents the next morning due to the staining effect of the drug and the generation of a stain on the teenager's person or the teen's clothes. In this case, the willingness to use the drug or lack thereof is a measure of psychological deterrence.

Such a deterrence may occur even if the drug is not visibly stained, and whether or not it is stained at all. It is possible for the deterrence to effect a potential user's decision to use on the basis that the drug is believe to be stained with a non-visible but fluorescent dye. It is also possible that a potential user would be deterred simply from the possibility that the drug is stained and choose not to use, regardless of whether the user believes the drug is stained.

In another example, the staining of solvent carriers of the methamphetamine product, such as water or alcohol, can deter the introduction of the drug to a person's beverage without their knowledge, particularly where the staining results in visible coloring. This can prevent people from accidentally becoming addicted to the drug in situations where the drug is ingested without that persons knowledge, such as where the drug is placed in that person's drink by another person. This can also prevent the drug from being used to "dope" others without their knowledge, such as in the common use of the so-called date rape drug. Such unknown doping also occurs through the mixing of illicit drugs, for example, when methamphetamine is mixed with cocaine. Stained methamphetamine will also discourage use of the drug as users are deterred from use by the obvious discoloration. Besides the increased risk of detection (even long after use), such discoloration raises concern regarding the quality of the product. Where the pure product is known to be white, a potential user may wonder what other impurities, possibly harmful impurities, may be present in a stained drug product. This change in appearance is also shown in FIG. 2.

For the ammonia trafficker, the staining effect of the vapor, makes it more difficult to initially obtain the liquid ammonia if one does not wish to be stained. As most thieves of liquid ammonia do not have access to sophisticated safety and transport equipment such as is used by authorized users, it is likely that while attempting to steal the liquid ammonia, liquid streams, droplets, vapor, or mist will be released under pressure from the tank, staining the would be thief, their clothing, the transport vessel and associated items, often including a vehicle in which the stolen liquid ammonia is being carried. Where the stain is obvious under visible light illumination, this stain may be readily detected by law enforcement as the thieves are making their getaway with the liquid ammonia, allowing them to be apprehended before they can sell such stolen ammonia, or even begin methamphetamine production. In another embodiment, the dye in ammonia solution is not obviously colored, so that it is unapparent to one who would attempt to steal the liquid ammonia that the material may or may not contain the dye until it is too late and the staining has occurred. Such an embodiment deters the theft of all anhydrous ammonia as there exists in the general consciousness of would be thieves a fear of potential staining, even if the dye is not included in solution.

In addition to making the production and use of methamphetamine a messier process, and thereby providing a psychological deterrent to such activities, in an embodiment, the inclusion of a tracer dye such as rhodamine WT in anhydrous ammonia will also make the production of methamphetamine more time consuming and costly, either by decreasing the resultant yield of methamphetamine produced using the solution of dye in ammonia, decreasing the resultant quality of methamphetamine, lowering its market price, or increasing the time and materials required to make the same amount of the same quality of methamphetamine as would be produced using pure liquid ammonia. The inclusion of rhodamine WT, other xanthene dye, or other dye may inhibit the necessary reactions required to form methamphetamine. Also as presented below in the Examples section with respect to rhodamine WT specifically, methamphetamine produced from ammonia including a xanthene dye is a product dissimilar in physical characteristics from methamphetamine produced without the dye present. Not only is the produced methamphetamine colored instead of white, but it is also not a flowable powder and is instead wet or oily. The step in production that would normally result in an essentially dry, white, powder within a few minutes, instead results in a gooey or gummy pink mass taking increased time and effort to filter when methamphetamine is made using a solution of rhodamine WT in ammonia. This wetness or oily character makes the drug product unappealing, difficult to manipulate, collect, and carry, and may alter the procedure by which one uses the drug to obtain the desired physiological effect. It may also inhibit the desired physiologic effect to some extent, as well. These results in the synthesis of methamphetamine when a solution of dye in ammonia is used result in physical deterrence through reduced or eliminated yields, or economic deterrence through more costly procedures required to obtain "clean" product, if such a result is possible after the stained product is produced. As discussed above and in Example 1 below, even small amounts of dye result in significant alteration of the characteristics of the methamphetamine produced. Because such small amounts result in such alteration, it may be particularly challenging to remove the dye from the ammonia to an extent that the dye does not interfere with the physical properties of the methamphetamine.

An additional result of the various deterrent effects of a dye in ammonia solution, is a certain security provided to those who legitimately store, transport, and use liquid ammonia. With knowledge that tanks may contain marking dye, someone who would steal from a legitimate user is more likely to find an easier target to steal from, or forego use of ammonia, to use a different product or material altogether, and in this way avoid the problems associated with detection of wrongful activity. This deterrent, then, eliminates either or both of the financial drain and bodily danger to legitimate users. Alternatively, while the staining may not deter completely certain thefts of ammonia, it may force those attempting such thefts to use more sophisticated methods, which are generally safer for everyone involved, including the victim, the thief, and those nearby. Further, in so much as there is benefit to knowing about a theft or attempted theft, the visible color staining of an embodiment, in particular, is an aid to legitimate user victims of theft. Rather than having to wait until a measurement indicates less ammonia present in a storage tank than expected, the victim of a theft is likely to know of the theft immediately upon viewing the area around the tank, due to the colored stain at the site of the theft. To the extent it is beneficial, a victim can even identify a theft or attempted theft from a distance due to the colored stain.

The addition of a dye to solid ammonium nitrate can also serve similar ends as those served by the dye in ammonia solution, that is, identification of individuals and hazardous conditions involved with misuse of the material. As well, deterrence in other circumstances related to the production of illicit drugs, such as where an attempt is made to convert ammonium nitrate to ammonia for use as described above, and in unrelated circumstances, such as the production of explosives. For example, those attempting to build explosives or bombs out of ammonium nitrate may be stained, which can facilitate the recognition and disruption of possible terrorist activities before they can be carried out. Further, a dye in ammonium nitrate can stain those attempting to convert the ammonium nitrate into anhydrous ammonia for their use in later methamphetamine production. While the dye may remain in the resultant ammonia product, providing all the benefits discussed above, one would see that even if it does not, dying of the ammonium nitrate can provide for a deterrent effect based on a staining effect caused by contact with the ammonium nitrate.

As a benefit essentially opposite of deterrence, where the presence of the stain is unknown and not visible under sunlight or white electric lights, but yet detectable, such as by fluorescence, there is provided a false sense of security to those who use a solution of dye in ammonia or illicit drugs produced therefrom. The benefit to society is in the fact that these users are now easier to detect because they are not highly alert and sensitive to potential detection.

The compositions, methods, and systems discussed herein are particularly useful with respect to solutions of dyes in ammonia to detect the presence or prior presence of ammonia. A reason for such particular utility is that a primary use of ammonia is as a fertilizer for agricultural production. In such an application it is fairly irrelevant if the land comprising a field used to grow agricultural products has applied to it a small quantity of a dye, so long as the dye is relatively safe with respect to animal and environmental health. While the compositions, methods, and systems disclosed herein are also useful with respect to solutions of dyes in other solvents such as alcohols, ethers, ketones, and other organic or inorganic solvents, especially those solvents that may be used in the production of controlled substances other than methamphetamine (i.e., substances regulated by federal law, such as are listed in Title 21 of the Code of Federal Regulations), or in other production methods for methamphetamine than the lithium reduction method, which relies on ammonia as a solvent, such other solvents are often used for purposes in which the presence of a dye is unwanted and perhaps detrimental. In sum, there is no reason that the compositions, methods, and systems disclosed herein are prohibited from being used with solvents other than ammonia as would be understood by one of ordinary skill in the art, such use just may not be as practical due to the predominant uses of the various other solvents.

EXAMPLES

The invention now will be described with respect to the following examples; however, the scope of the present invention is not intended to be limited thereby.

Example 1

In a controlled laboratory setting, 12 microliters of the commercial product marketed as "KeyAcid™ Rhodamine WT" and manufactured by Keystone Analine Corporation of Chicago, Ill., which is a 21.2% w/w solution of rhodamine WT in water, and 300 mL of anhydrous ammonia were combined in a flask. This is approximately equivalent to 2 oz of KeyAcid™ Rhodamine WT in one ton of liquid anhydrous ammonia. The mixture was stirred until a solution formed that had a very slight yellow tint. The solvation of rhodamine WT in ammonia transformed the rhodamine WT into a nearly colorless composition. The surface of each piece of equipment used in this process, however, was visibly stained a light pink in areas exposed to the ammonia and from which the ammonia had evaporated. The solution was also purposefully put in contact with various additional equipment and materials, including metal screwdriver heads, concrete, and paper. All exposed equipment and materials were visibly stained pink upon evaporation of the anhydrous ammonia. During the mixing process, some of the mixture unintentionally contacted items, including protective gloves and the hands of the researchers who were performing the mixing. These additional items were also visibly stained pink.

The solution of dye in ammonia was added to 2 grams of pure pharmaceutical grade ephedrine in a 500 mL beaker. The contents of the flask were stirred to dissolve the ephedrine. Any material that came into contact with this solution, including the flask when the flask was emptied, was also visibly stained pink upon evaporation of the ammonia solvent. The visible pink stain on the flask was transferred to a sponge when the flask was washed.

Lithium metal was added to the ephedrine solution. This mixture was heated to carry out a so-called "Birch" reaction. During the Birch reaction, materials contacted by the mixture were not stained. It is believed that the lack of a stain at this stage may be due to a reduction of the rhodamine WT to a colorless composition.

Evaporation of the ammonia from the Birch reaction mixture left a free base form of methamphetamine. In order to purify it, the free base methamphetamine was dissolved into a liquid ether and converted to the hydrochloride salt by bubbling hydrogen chloride gas through the solution. The methamphetamine salt precipitated from solution. During this process plastic tubes used to carry the hydrogen chloride gas into the dissolved methamphetamine were visibly stained pink as was the beaker.

The methamphetamine salt product was filtered through a coffee filter to retain the methamphetamine. The coffee filter used for this filtration along with the resultant product is shown in the picture of FIG. 3. Two things were observed. First, the coffee filter and resulting product are both stained pink. Further, the filtration does not occur easily because instead of a rapidly-drying, clear crystal being formed, the product was a pink sludge, which was difficult to filter and dry. This pink sludge (methamphetamine) visibly stained objects with which it came into contact pink, including plastic storage bags.

Example 2

A researcher's living human skin was exposed to a small amount of a solution of rhodamine WT and was visibly stained pink. The skin was then repeatedly washed until the dye was no longer visible to the unaided human eye. The skin was then observed under irradiation by a hand-held UV light which showed the originally stained area still indicated by fluorescence. Fluorescence was still visible on the skin two weeks later when exposed to UV light after normal activity and washing by the researcher. When a more concentrated solution of the dye was used in a similar fashion, fluorescence was still visible 4–6 weeks after exposure.

Example 3

Methamphetamine was generated using liquid anhydrous ammonia containing rhodamine WT as a dye in a similar manner to that discussed in Example 1. Physio-chemical nvestigation of the methamphetamine led to a finding that some dye resided on the outer surface of methamphetamine crystals. To attempt to remove the dye from the resultant methamphetamine, the crystals were washed with one of: water, acetone, toluene, petroleum ether or xylenes. In all cases either the methamphetamine and dye dissolved in the washing agent and the resultant mixture would stain objects it came into contact with, or neither the methamphetamine nor dye dissolved. The methamphetamine was recrystalized from various solutions containing dyed methamphetamine and at least one of: alcohol, toluene, xylenes and petroleum ether. The resulting recrystalizations still showed obvious staining from the dye indicating that dissolution and recrystalization did not result in removal of the dye.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method for staining a human being who comes into contact with liquid-state ammonia, the method comprising:
   introducing into liquid-state ammonia a xanthene dye to form a solution;
   having said human being come into contact with said solution; and
   allowing conversion of some of said liquid-state ammonia from a liquid to a gas while said human being is in contact with said solution, said dye creating a stain on said human being in contact with said liquid-state ammonia upon said conversion.

2. The method of claim 1 wherein said xanthene dye is a fluorone.

3. The method of claim 1 wherein said xanthene dye is a pyronin.

4. The method of claim 1 wherein said xanthene dye is a rhodamine.

5. The method of claim 1 wherein said xanthene dye is rhodamine WT.

6. The method of claim 1 wherein said xanthene dye is fluorescein.

7. The method of claim 1 wherein the step of detecting said stain is capable of being performed by an unaided human eye.

8. The method of claim 1 wherein said stain is colored under visible light illumination.

9. The method of claim 1 wherein said step of detecting said stain comprises said stain fluorescing in response to illumination by ultraviolet (UV) light.

10. The method of claim 1 wherein said xanthene dye is introduced at a rate of between about to 1 to 100 parts per million parts of ammonia on a weight to weight basis.

11. A method of staining materials used in the production of methamphetamine, the method comprising:
    providing a solution of a xanthene dye in ammonia;
    using said solution in the production of methamphetamine, thereby generating production byproducts that comprise said solution;
    staining materials contacted by at least one of said solution, said byproducts, or said methamphetamine; and
    detecting said staining on said materials;
    wherein said staining can be detected even in the absence of any one or more of said solution, said byproducts, and said methamphetamine.

12. The method of claim 11 wherein said xanthene dye is a fluorone.

13. The method of claim 11 wherein said xanthene dye is a pyromin.

14. The method of claim 11 wherein said xanthene dye is a rhodamine.

15. The method of claim 11 wherein said xanthene dye is rhodamine WT.

16. The method of claim 11 wherein said xanthene dye is fluorescein.

17. The method of claim 11 wherein said staining is visible to the naked eye.

18. The method of claim 11 wherein said staining is colored under visible light illumination.

19. The method of claim 11 wherein said staining fluoresces in response to illumination by ultraviolet (UV) light.

20. The method of claim 11 further comprising the step of:
    having said xanthene dye survive said production of said methamphetamine, thereby staining said methamphetamine.

21. The method of claim 20 wherein at least some of said xanthene dye resides on the surface of said methamphetamine.

22. The method of claim 20 wherein said xanthene dye stains materials which come into contact with said methamphetamine.

23. The method of claim 20 wherein said staining of said methamphetamine comprises staining visible to the naked eye.

24. The method of claim 20 wherein said staining of said methamphetamine is colored under illumination by visible light.

25. The method of claim 20 wherein said staining of said methamphetamine comprises a stain that fluoresces in response to illumination by ultraviolet (UV) light.

26. A method for deterring the theft of liquid-state ammonia comprising:
    providing liquid-state ammonia in a vessel;
    adding a xanthene dye to said liquid-state ammonia;
    forming a solution of said ammonia and said dye, said solution generating a stain on objects that contact said solution; and
    indicating that said vessel includes said solution.

27. The method of claim 26 wherein said solution is visibly distinct from said liquid-state ammonia.

28. The method of claim 26 wherein said liquid-state ammonia comprises anhydrous ammonia.

29. The method of claim 28 wherein said anhydrous ammonia is stored under pressure.

30. The method of claim 26 wherein said dye comprises a fluorescing dye.

31. The method of claim 26 wherein said dye comprises a rhodamine dye.

32. The method of claim 26 wherein said step of forming a solution includes forming a homogeneous mixture.

33. The method of claim 26 wherein said step of indicating comprises labeling said vessel with a warning sign.

34. The method of claim 33 wherein said warning sign is a sticker placed on said vessel.

35. The method of claim 26 wherein said vessel is a pressurized tank.

36. A method of generating stained methamphetamine, the method comprising:
  providing a solution of a xanthene dye in ammonia;
  using said solution in the production of said methamphetamine and
  having said xanthene dye exhibit color in said resultant methamphetamine.

37. The method of claim 36 wherein said stained methamphetamine is able to stain materials contacted by said stained methamphetamine.

38. The method of claim 37 wherein said materials comprise human skin.

* * * * *